United States Patent [19]
Place

[11] Patent Number: 5,407,688
[45] Date of Patent: *Apr. 18, 1995

[54] COMPOSITIONS AND METHODS FOR TREATING GASTROINTESTINAL DISORDERS

[75] Inventor: Geoffrey Place, Cincinnati, Ohio

[73] Assignee: The Procter & Gamble Company, Cincinnati, Ohio

[*] Notice: The portion of the term of this patent subsequent to Apr. 4, 2012 has been disclaimed.

[21] Appl. No.: 970,595

[22] Filed: Oct. 30, 1992

Related U.S. Application Data

[63] Continuation of Ser. No. 426,482, Oct. 23, 1989, abandoned, which is a continuation of Ser. No. 23,596, Mar. 9, 1987, abandoned.

[51] Int. Cl.$^6$ .................. A61K 33/24; A61K 31/555; A61K 31/415; A61K 31/34
[52] U.S. Cl. ...................... 424/653; 514/184; 514/188; 514/400; 514/471
[58] Field of Search ............... 514/184, 400, 471, 188; 424/653

[56] References Cited

U.S. PATENT DOCUMENTS

| | | | |
|---|---|---|---|
| 4,148,912 | 4/1979 | Vincent et al. | 424/295 |
| 4,333,922 | 6/1982 | Herschler | 424/89 |
| 4,942,181 | 7/1990 | Riede | 514/730 |
| 4,959,384 | 9/1990 | Kraft et al. | 514/390 |
| 5,008,256 | 4/1991 | Clitherow | 514/184 |

FOREIGN PATENT DOCUMENTS

| | | | |
|---|---|---|---|
| 206625 | 12/1986 | European Pat. Off. | A61K 33/00 |
| 206626 | 12/1986 | European Pat. Off. | A61K 33/00 |
| 206627 | 12/1986 | European Pat. Off. | A61K 31/60 |
| 219912 | 4/1987 | European Pat. Off. | A61K 31/415 |
| 282131 | 9/1988 | European Pat. Off. | |
| 282132 | 9/1988 | European Pat. Off. | |
| 2054373 | 2/1981 | United Kingdom | A61K 45/06 |
| 86/05981 | 10/1986 | WIPO | A61K 31/29 |

OTHER PUBLICATIONS

Ward et al., "A Double Blind Trial of the Treatment of Gastric Ulcers with a Combination of DeNol and Cimetidine", Adelaide Scientific Meeting, 1979, Programme Abstracts of Papers, Australian Mineral Foundation, Oct. 8-9; p. A30.

Goldenberg et al., "Protective Effect of Pepto-Bismol Liquid on the Gastric Mucosa of Rats", Gastroenterology, 69(3), pp. 636-640 (1975).

Vantrappen et al., "Randomized Open Controlled Trial of Colloidal Bismuth Subcitrate Tablets and Cimetidine in the Treatment of Duodenal Ulcers", Gut, 21(4), pp. 329-333 (1980).

Wieriks et al., "Pharmacological Properties of Colloidal Bismuth Subcitrate (CBS, DE-NOL®)", Scand. J. Gastroenterol., 17, Supplement 80, pp. 11-16 (1982).

Koo et al., "Selective Coating of Gastric Ulcer by Tripotassium Dicitrato Bismuthate in the Rat", Gastroenterology, 82, pp. 864-870 (1982).

Lu et al., "Effect of Furaxon and its Analogs on Gastrointestinal Propulsion in Mice", Beijing Yixueyuan Xuebao, 15, pp. 185-187 (1983).

Marshall et al., "Unidentified Curved Bacilli in the Stomach of Patients with Gastritis and Peptic Ulceration", Lancet, 1, pp. 1311-1315 (Jun. 16, 1984).

McLean et al., "Microbes, Peptic Ulcer and Relapse Rates with Different Drugs", Lancet, 2, pp. 525-526 (Sep. 1, 1984).

(List continued on next page.)

Primary Examiner—Zohreh Fay
Attorney, Agent, or Firm—Kim William Zerby; Douglas C. Mohl; Jacobus C. Rasser

[57] ABSTRACT

The present invention relates to pharmaceutical compositions useful for treating or preventing gastrointestinal disorders. These compositions comprise a campylobacter-inhibiting antimicrobial agent such as nitrofurantoin and bismuth subsalicylate, and a histamine-2 receptor blocking anti-secretory agent such as cimetidine.

The present invention further relates to methods for treating or preventing gastrointestinal disorders in humans or lower animals by administering a campylobacter-inhibiting antimicrobial agent and a histamine-2 receptor blocking anti-secretory agent.

45 Claims, No Drawings

OTHER PUBLICATIONS

Hislop et al., "Histological Improvement of Active Chronic Gastritis in Patients Treated with De-Nol", *Australia and New Zealand Journal of Medicine*, 14, p. 907 (1984).

Lam et al., "Randomised Crossover Trial of Tripotassium Dicitrato Bismuthate Versus High Dose Cimetidine for Duodenal Ulcers Resistant to Standard Dose of Cimetidine", *Gut*, 25, pp. 703–706 (1984).

Zeng Zhi-Tian et al., "Double-Blind Short-Term Trial of Furazolidone in Peptic Ulcer", *Lancet*, 1, pp. 1048–1049 (May 4, 1985).

Piper, "Bacteria, Gastritis, Acid Hyposecretion and Peptic Ulcer", *The Medical Journal of Australia*, 142, p. 431 (1985).

Pinkard et al., "Campylobacter-Like Organisms From the Human Stomach—Detection, Characterization, and In Vitro Susceptibilities", Campylobacter III (Pearson et al., editors; 1985), 171–172.

Goodwin et al., "The Association of Campylobacter Pyloridis with Gastritis, and Its In Vitro Sensitivity to Antibiotics and Anti-Ulcer Agents", *Australia and New Zealand Journal of Medicine*, 15, (1 Supplement 1), p. 153 (1985).

Lambert et al., "Campylobacter-Like Organisms (CLO)—In Vivo and In Vitro Susceptibility to Antimicrobial and Anti-Ulcer Therapy", *Gastroenterology*, 88, p. 1462 (1985).

McNulty et al., "Successful Therapy of Campylobacter Pyloridis Gastritis", *Gastroenterology*, 90, p. 1547 (1986).

Goodwin et al., "The Minimum Inhibitory and Bactericidal Concentrations of Antibiotics and Anti-Ulcer Agents Against Campylobacter Pyloridis", *Journal of Antimicrobial Chemotherapy*, 17, pp. 309–314 (1986).

Hirschl et al., "Sensitivity of Campylobacter Pyloridis to Antimicrobials and Anti-Ulcer Drugs", *Z. Antimikrob Antineoplast. Chemother.*, 4 (2), pp. 45–49 (1986).

Salmon, "Combination Treatment: Colloidal Bismuth Subcitrate with $H_2$-Antagonist", *Digestion*, 37, pp. 42–46 (1987).

U.S. Pat. Ser. No. 07/821,244 filed Jan. 10, 1992.

Peterson et al., *Gastroenterology*, 1979, 77, 1015–1020.

Martin et al., *The Lancet*, 1981, 7–10.

*Gut*, 1992, vol. 33, pp. 179–183.

*Gut*, 1984, 25, pp. 697–702.

*Pharmac. Ther.*, 1984, 26, pp. 221–234.

Letter by M. C. Brooks dated 11 Jun. 1991, during examination of European Patent No. 206,626.

Letter by J. L'Helgoualch dated 8 Dec. 1992, during examination of European Patent Application No. 88200396.5, Publication No. 282,131.

*Deutsche Med. Wochenschrift*, vol. 112, No. 37, Sep. 1987, pp. 1407–1411.

*Wiener Klinische Wochenschrift*, vol. 99, No. 14, 17 Jul. 1987, pp. 493–497.

*Chemical Abstracts*, vol. 107, No. 5, 34d Aug. 1987, p. 397, Abstract No. 36471w.

COMPOSITIONS AND METHODS FOR TREATING GASTROINTESTINAL DISORDERS

This is a continuation of application Ser. No. 426,482 filed Oct. 23, 1989, now abandoned, which is a continuation of application Ser. No. 023,596, filed on Mar. 9, 1987, abandoned.

The present invention relates to pharmaceutical compositions useful for treating or preventing gastrointestinal disorders. These compositions comprise a campylobacter-inhibiting antimicrobial agent and a histamine-2 receptor blocking anti-secretory agent. The present invention further relates to treating or preventing gastrointestinal disorders in humans or lower animals by administering a campylobacter-inhibiting antimicrobial agent and a histamine-2 receptor blocking anti-secretory agent. These methods may involve either concurrent or non-concurrent administration of the campylobacter-inhibiting antimicrobial agent and the histamine-2 receptor blocking anti-secretory agent.

Factors adversely affecting the function of the gastrointestinal system in humans are exceedingly varied in their nature. Such disorders may arise in the upper or lower gastrointestinal tracts or both. There is a broad range of causes of gastrointestinal disorders, including genetic, physiological, environmental, and psychogenic factors. Accordingly, the diagnosis and management of these disorders can be exceptionally difficult. A detailed discussion of gastrointestinal tract functions, disorders, causes, and treatments can be found in Spiro, *Clinical Gastroenterology* (3d. edition 1983).

Among the chronic disorders of the upper gastrointestinal tract are those which fall under the general categories of gastritis and peptic ulcer disease. Gastritis is, by definition, typified by an inflammation of the stomach mucosa. In practice, though, the disorder is manifested by a broad range of poorly-defined, and heretofore inadequately treated, symptoms such as indigestion, "heart burn", dyspepsia and excessive eructation. A general discussion of gastritis appears in B. J. Marshall and J. R. Warren, "Unidentified Curved Bacilli in the Stomach of Patients with Gastritis and Peptic Ulceration", *The Lancet*, (1984), pp. 1311-1315, and in R. Greenlaw, et al., "Gastroduodenitis, A Broader Concept of Peptic Ulcer Disease", Digestive Diseases and Sciences, Vol. 25 (1980), pp. 660-672.

Peptic ulcers are lesions of the gastrointestinal tract lining, characterized by loss of tissue due to the action of digestive acids and pepsin. It has been generally held that peptic ulcers are caused either by gastric hypersecretion, or (more often) by decreased resistance of the gastric lining to digestive acids and pepsin. The medical literature is replete with methods for treating ulcers, including modification of the diet, surgical removal of the lesions, and the use of drugs. Such drugs include: antacids, which serve to counteract excess gastric secretions; anticholinergics, which reduce acid secretion; $H_2$ antagonists, which also block the release of gastric acids; prostaglandins, which increase the resistance of the gastric lining to digestive fluids, and may also inhibit acid secretion; prokinetic agents, which enhance gastrointestinal tract motility; and compositions which form protective barriers over gastric lesions. Prescription and non-prescription drug therapies are generally described in Garnet, "Antacid Products", *Handbook of Non-prescription Drugs*, 7th edition (1982), Chapter 3.

Regardless of the particular drug composition used in treating gastrointestinal disorders, such as gastritis or peptic ulcer disease, the treatment is often imprecise and incomplete. Actual "cures", i.e., successful treatment resulting in total remission of disease, are very often not effected. See A. J. McLean, et al., "Cyto-protective Agents and Ulcer Relapse", 142 *The Medical Journal of Australia*, Special Supplement S25-S28 (1985). Furthermore, many conventional treatments may render subject hypochlorhydric (i.e., with low levels of hydrochloric acid in the stomach) which may predispose them to other disorders, e.g., gastrointestinal infection, halitosis, and gastric carcinomas.

The treatment of gastrointestinal disorders with histamine-2 (hereinafter "$H_2$") receptor blocking anti-secretory agents is well-known in the art. For example, cimetidine (marketed under the tradename Tagamet ®; Smith Kline & French Laboratories, Philadelphia, Pa.) is an $H_2$ receptor block anti-secretory agent widely used in the treatment of gastric ulcers. This compound, as well as others of this type, are thought to act by blocking the histamine receptors within the stomach mucosa (labeled $H_2$ receptors, to distinguish from those histamine receptors generally associated with allergic response) thereby preventing histamine molecules from signaling the stomach cells to secrete acid. $H_2$ receptor blocking agents which are either more potent and/or longer acting than cimetidine (e.g., ranitidine) are also well-known. (See *C&E News*, Apr. 12, 1982, pp. 24-26). However, while $H_2$ receptor blocking anti-secretory agents have demonstrated effectiveness in treating gastrointestinal disorders and therefore are widely prescribed for this purpose, their utility is questioned in light of the poor long-term outcomes associated with their use (e.g., high relapse rate associated with cimetidine treatment of gastric ulcers; see *The Lancet*, Sep. 1, 1984, pp. 525-526).

The treatment of gastrointestinal disorders with agents having antimicrobial properties, including antimicrobial activity against *Campylobacter pyloridis*, is also known in the art. For example, furazolidone has been used in the treatment of ulcers (*The Lancet*, May 4, 1985, pages 1048-1049); bismuth subcitrate (DeNol; sold by Gist-Brocades, N.V.) has been used to treat gastritis and/or duodenal ulcers in patients having *Campylobacter pyloridis* infections (*Gastroenterology*, 88(5 Part 2), page 1462 (1985); *Aust. and N.Z.J. of Medicine*, 14, p. 907 (1984)); and bismuth-subsalicylate (Pepto-Bismol; sold by The Procter & Gamble Company) has been used to treat gastritis in patients having *Campylobacter pyloridis* infection (*Gastroenterology*, 90, page 1547 (1986)).

Recent research has noted an association between gastritis, peptic ulceration, and the presence of *Campylobacter pyloridis* and campylobacter-like organisims (*The Lancet*, Jun. 16, 1984, pages 1311-1315). This has led to speculation that the high relapse rate observed when treating ulcers with cimetidine is the result of cimetidine allowing healing but adversely affecting the subsequent ability of the gastrointestinal tract to resist ulcerogenic activity of a pathogenic agent (*The Lancet*, Sep. 1,1984, pages 525-526). However, subsequent research indicates that cimetidine inhibits *Campylobacter pyloridis* growth at low concentrations (*Z. Antimikrob. Antineoplast. Chemother.*, 4 (2), pages 45-49 (1986); *J. Antimicrob. Chemother.*, 17 (3), pages 309-314 (1986)). Furthermore, preliminary findings support the concept that campylobacter-like organisms are not important in the etiology of duodenal ulcer disease (*Gastroenterology*, 88 (5 part 2), p. 1462 (1985)). Thus, it is currently not clear whether the high relapse rate associated with cimetidine treatment is, in fact, due to an adverse affect on the ability of the gastrointestinal tract to resist pathogenic agents.

Clearly, there remains a continuing need to identify new compositions which are effective for treating and preventing gastrointestinal disorders. The present invention provides such novel pharmaceutical compositions, comprising campylobacter-inhibiting antimicrobial agents and $H_2$ receptor blocking anti-secretory agents, useful for treating and preventing gastrointestinal disorders. While, as noted hereinbefore, $H_2$ receptor blocking anti-secretory agents and antimicrobial agents which have activity against *Campylobacter pyloridis* are individually known for treating and/or preventing gastrointestinal disorders, the compositions and methods of the present invention combine these two agents into compositions and methods which are surprisingly effective for treating and preventing gastrointestinal disorders.

It is therefore an object of the present invention to provide novel pharmaceutical compositions comprising campylobacter-inhibiting antimicrobial agents and $H_2$ receptor blocking anti-secretory agents. It is a further object to provide improved methods for treating or preventing gastrointestinal disorders in humans or lower animals. An additional object is to provide compositions and methods which have improved ability to treat and prevent gastritis and gastrointestinal ulcers, and to improve the long-term outcomes of ulcer treatments. Finally, an object of the present invention is to reduce the incidence of gastritis following ulcer treatment with $H_2$ receptor blocking anti-secretory agents and/or reduce the ulcer relapse rate observed following ulcer treatment with $H_2$ receptor blocking anti-secretory agents.

These and other objects will become readily apparent from the detailed description which follows.

SUMMARY OF THE INVENTION

The present invention relates to pharmaceutical compositions useful for treating or preventing gastrointestinal disorders. These compositions comprise a campylobacter-inhibiting antimicrobial agent (e.g., nitrofurantoin; bismuth subsalicylate), and an $H_2$ receptor blocking anti-secretory agent (e.g., cimetidine; ranitidine).

The present invention further relates to methods for treating or preventing gastrointestinal disorders in humans or lower animals. These methods comprise administering to a human or lower animal in need of such treatment or prevention a safe and effective amount of a campylobacter-inhibiting antimicrobial agent and a safe and effective amount of a $H_2$ receptor blocking anti-secretory agent.

DETAILED DESCRIPTION OF THE INVENTION

Campylobacter-inhibiting Antimicrobial Agents

The pharmaceutical compositions of the present invention essentially comprise a campylobacter-inhibiting antimicrobial agent. The term "campylobacter-inhibiting antimicrobial agent", as used herein, means any naturally-occurring, synthetic or semi-synthetic compound or composition, or mixture thereof, which is safe for human use as used in the compositions and methods of the present invention, and is effective in killing or substantially inhibiting the growth of campylobacter-like organisms, e.g., *Campylobacter pyloridis*, when used in the compositions and methods of this invention. Such campylobacter-like organisms include those described in J. R. Warren and B. J. Marshall, "Unidentified Curved Bacilli on Gastric Epithelium in Active Chronic Gastritis", *The Lancet*, pages 1273–1275 (1983), and G. Kasper and N. Dickgiesser, "Isolation from Gastric Epithelium of Campylobacter-like Bacteria that are Distinct from '*Campylobacter pyloridis*'", *The Lancet*, pages 111–112 (1985), the disclosures of both these references being incorporated herein by reference in their entirety. The effectiveness of antimicrobial agents to kill or substantially inhibit the growth of campylobacter-like organisms for use in the present invention may be demonstrated using the various in vitro or in vivo assays known to those skilled in the art as described more fully hereinafter.

Campylobacter-inhibiting antimicrobial agents useful herein include antibiotics, such as penicillin G, gentamicin, erythromycin, and tetracycline; the sulfonamides; nitrofurans, such as nitrofurazone, nitrofurantoin, and furazolidone; and metronidazole, tinidazole, and nimorazole. Campylobacter-inhibiting antimicrobial agents are described in the following publications, incorporated by reference herein in their entirety: Gastroenterology, 88(5 Part 2), page 1462 (1985); *Aust. and N.Z.J. of Medicine*, 15(1 Suppl. 1), page 153 (1985); *Z Antimikrob. Antineoplast. Chemother.*, 4(2), pages 45–49 (1986); *J. Antimicrob. Chemother.*, 17(3), pages 309–314; (1986); *Aust. and N.Z.J. of Medicine*, 14, p. 907 (1984); *Gastroenterology*, 90, page 1547 (1986); *The Lancet*, Sep. 1, 1984, pages 525–526; *Remington's Pharmaceutical Sciences* (15th Edition; 1975); F. H. Meyers, et. al. *Review of Medical Pharmacology* (7th Edition; 1980); *Gaddum's Pharmacology* (8th Edition; 1978); and A. Goodman, et al., *The Pharmacological Basis of Therapeutics* (6th Edition; 1980).

Preferred campylobacter-inhibiting antimicrobial agents for use herein are nitrofurans having the following chemical structure:

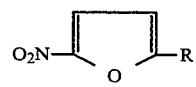

wherein R is hydrogen or an organic radical, or the salts or hydrates thereof. Antibacterial nitrofuran are disclosed in the following U.S. Patents, all of which are incorporated herein by reference in their entirety: U.S. Pat. No. 2,319,481 issued to Stillman, Scott & Clampit on May 18, 1943; U.S. Pat. No. 2,416,233 issued to Stillman & Scott on Feb. 18, 1947; U.S. Pat. No. 2,416,234 issued to Stillman & Scott on Feb. 18, 1947; U.S. Pat. No. 2,416,235 issued to Stillman & Scott on Feb. 18, 1947; U.S. Pat. No. 2,416,236 issued to Stillman & Scott on Feb. 18, 1947; U.S. Pat. No. 2,416,237 issued to Stillman & Scott on Feb. 18, 1947; U.S. Pat. No. 2,416,238 issued to Stillman & Scott on Feb. 18, 1947; U.S. Pat. No. 2,416,239 issued to Stillman & Scott on Feb. 18, 1947; U.S. Pat. No. 2,599,509 issued to Austin & Hastie on Jun. 3, 1952; U.S. Pat. No. 2,610,181 issued to Hayes on Sep. 9, 1952; U.S. Pat. No. 2,626,258 issued to Ward on Jan. 20, 1953; U.S. Pat. No. 2,656,350 issued to Ward & Gever on Oct. 20, 1953; U.S. Pat. No. 2,663,710 issued to Hayes on Dec. 22, 1953; U.S. Pat. No. 2,702,292 issued to Hayes on Jan. 15, 1955; U.S. Pat. No. 2,726,241 issued to Gever & Ward on Dec. 6, 1955; U.S. Pat. No. 2,742,462 issued to Gever on Apr. 17, 1956; U.S. Pat. No. 2,746,960 issued to Gever & Michels on May 22, 1956; U.S. Pat. No. 2,759,932 issued to Ebetino, Gever & Hayes on Aug. 21, 1956; U.S. Pat. No. 2,776,979 issued to Michels on Jan. 8, 1957; U.S. Pat. No. 2,798,068 issued to Gever on Jul. 2, 1957; U.S. Pat. No. 2,802,002 issued to Gever Aug. 6, 1957; U.S. Pat. No. 2,808,414 issued to Ward on Oct. 1, 1957; U.S. Pat. No. 2,828,309 issued to Gever on Mar. 25, 1958; U.S. Pat. No. 2,830,046 issued to Hayes on Apr. 8, 1958; U.S. Pat. No. 2,830,047 issued to Hayes on Apr. 8, 1958; U.S. Pat. No. 2,847,416 issued to Gever on Aug. 12, 1958; U.S. Pat. No. 2,847,424 issued to Ward on Aug. 12, 1958; U.S. Pat. No. 2,890,982 issued to Natt on Jun. 16, 1959; U.S. Pat. No. 2,906,752 issued to Howard on Sep. 29, 1959; U.S. Pat. No. 2,908,689 issued to Gever on Oct. 13, 1959; U.S. Pat. No. 2,920,074 issued to Michels on Jan. 5, 1960; U.S. Pat. No. 2,943,019 issued to Natt on Jun. 28, 1960; U.S. Pat. No. 2,980,704 issued to Gever on Apr. 18, 1961; U.S. Pat. No. 3,001,992 issued to Bellamy, Hayes & Michels on Sep. 26, 1961; U.S. Pat. No. 3,007,846 issued to Gever & Vincent on Nov. 7, 1961; U.S. Pat. No. 3,041,334 issued to Klein on Jun. 26, 1962; U.S. Pat. No. 3,043,853 issued to Ebetino on Jul. 10, 1962; U.S. Pat. No. 3,075,877 issued to Johnson on Jan. 29, 1963; U.S. Pat. No. 3,075,972 issued to Michels on Jan. 29, 1963; U.S. Pat. No. 3,075,973 issued to Michels on Jan. 29, 1963; U.S. Pat. No. 3,075,974 issued to Michels on Jan. 29, 1963; U.S. Pat. No. 3,076,805 issued to Michels on Feb. 5, 1963; U.S. Pat. No. 3,091,611 issued to Howard on May 28, 1963; U.S. Pat. No. 3,096,347 issued to Wright on Jul. 2, 1963; U.S. Pat. No. 3,097,202 issued to Michels on Jul. 9, 1963; U.S. Pat. No. 3,105,834 issued to Wei on Oct. 1, 1963; U.S. Pat. No. 3,108,122 issued to Ebetino on Oct. 22, 1963; U.S. Pat. No. 3,110,649 issued to Johnson on Nov. 12, 1963; U.S. Pat. No. 3,110,713 issued to Spencer on Nov. 12, 1963; U.S. Pat. No. 3,110,714 issued to Wright on Nov. 12, 1963; U.S. Pat. No. 3,121,083 issued to Howard on Feb. 11, 1964; U.S. Pat. No. 3,127,420 issued to Ebetino on Mar. 31, 1964; U.S. Pat. No. 3,138,593 issued to Burch on Jun. 23, 1964; U.S. Pat. No. 3,139,431 issued to Hayes on Jun. 30, 1964; U.S. Pat. No. 3,141,878 issued to Hellinghuizer on Jul. 21, 1964; U.S. Pat. No. 3,141,889 issued to Ebetino on Jul. 21, 1964; U.S. Pat. No. 3,149,119 issued to Ebetino on Sep. 15, 1964; U.S. Pat. No. 3,157,645 issued to Spencer on Nov. 17, 1964; U.S. Pat. No. 3,159,654 issued to Ward on Dec. 1, 1964; U.S. Pat. No. 3,164,595 issued to Burch & Benjamin on Jan. 5, 1965; U.S. Pat. No. 3,169,970 issued to Snyder on Feb. 16, 1965; U.S. Pat. No. 3,178,453 issued to Snyder on Apr. 13, 1965; U.S. Pat. No. 3,196,165 issued to Burch on Jul. 20, 1965; U.S. Pat. No. 3,206,461 issued to Ebetino & Gever on Sep. 14, 1965; U.S. Pat. No. 3,232,956 issued to Benjamin on Feb. 1, 1966; U.S. Pat. No. 3,254,075 issued to Ebetino on May 31, 1966; U.S. Pat. No. 3,260,732 issued to Snyder on Jul. 12, 1966; U.S. Pat. No. 3,272,840 issued to Benjamin on Sep. 13, 1966; U.S. Pat. No. 3,277,082 issued to Benjamin on Oct. 4, 1966; U.S. Pat. No. 3,277,110 issued to Burch on Oct. 4, 1966; U.S. Pat. No. 3,314,947 issued to Benjamin on Apr. 18, 1967; U.S. Pat. No. 3,324,122 issued to Burch on Jun. 6, 1967; U.S. Pat. No. 3,335,140 issued to Burch on Aug. 8, 1967; U.S. Pat. No. 3,335,141 issued to Burch on Aug. 8, 1967; U.S. Pat. No. 3,350,397 issued to Burch on Oct. 31, 1967; U.S. Pat. No. 3,367,931 issued to Snyder on Feb. 6, 1968; U.S. Pat. No. 3,367,932 issued to Snyder on Feb. 6, 1968; U.S. Pat. No. 3,374,239 issued to Burch on Mar. 19, 1968; U.S. Pat. No. 3,386,995 issued to Ebetino on Jun. 4, 1968; U.S. Pat. No. 3,391,155 issued to Benjamin on Jul. 2, 1968; U.S. Pat. No. 3,407,195 issued to Snyder on Oct. 22, 1968; U.S. Pat. No. 3,427,329 issued to Burch on Feb. 11, 1969; U.S. Pat. No. 3,446,802 issued to Michels on May 27, 1969; U.S. Pat. No. 3,450,708 issued to Burch on Jun. 17, 1969; U.S. Pat. No. 3,471,510 issued to Benjamin on Oct. 7, 1969; U.S. Pat. No. 3,485,830 issued to Snyder on Dec. 23, 1969; U.S. Pat. No. 3,542,784 issued to Burch on Nov. 24, 1970; U.S. Pat. No. 3,660,384 issued to Johnson on May 2, 1972; U.S. Pat. No. 3,723,477 issued to Pelosi on Mar. 27, 1973; U.S. Pat. No. 3,748,326 issued to Schwan & White on Jul. 24, 1973; U.S. Pat. No. 3,770,740 issued to Burch on Nov. 6, 1973; U.S. Pat. No. 3,808,203 issued to Snyder on Apr. 30, 1974; U.S. Pat. No. 3,808,204 issued to Snyder on Apr. 30, 1974; U.S. Pat. No. 3,808,211 issued to Benjamin on Apr. 30, 1974; U.S. Pat. No. 3,822,255 issued to Snyder on Jul. 2, 1974; U.S. Pat. No. 3,905,975 issued to Schwan on Sep. 16, 1975; U.S. Pat. No. 3,914,220 issued to Snyder on Oct. 21, 1975; U.S. Pat. No. 3,980,664 issued to Alaimo on Sep. 14, 1976; and U.S. Pat. No. 4,012,409 issued to Alaimo on Mar. 15, 1977.

Antibacterial nitrofurans are also disclosed in the following references, all of which are hereby incorporated by reference in their entirety: Miura, K., and H. K. Reckendorf, "The Nitrofurans", *Progress in Medicinal Chemistry*, G. P. Ellis and G. B. West (ed.), Plenum Press, New York, N.Y., (1967), Vol. 5, pp. 320–381; Grunberg, E., and E. H. Titsworth, "Chemotherapeutic Properties of Heterocyclic Compounds: Monocyclic Compounds with Five-Membered Rings", *Annual Review of Microbiology*, M. P. Starr, J. L. Ingraham and S. Raffel (ed.), Annual Reviews Inc., Palo Alto, Calif., (1973), Vol. 27, pp. 317–346; "Nitrofurans: Chemistry, Metabolism, Mutogenesis, and Carcinogenesis", *Carcinogenesis*, Vol. 4, G. T. Bryan (ed.), Raven Press, New York, N.Y., (1978); "Antibacterial Agents, Nitrofurans", *Kirk-Othmer: Encyclopedia of Chemical Technology*, John Wiley & Sons, Inc., Third Edition, Vol. 2, pp. 790–794; and McCalla, D. R., "Nitrofurans", *Mechanism of Action of Antibacterial Agents*, F. E. Hahn (ed.), Springer-Verlag, New York, N.Y. (1979), pp. 176–213.

Antibacterial nitrofurans preferred as components of the present invention include those wherein R is

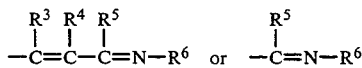

wherein $R^3$, $R^4$ and $R^5$ are H or lower alkyl; and $R^6$ is an organic radical, or salts or hydrates thereof.

More preferred are antibacterial nitrofurans conforming to the above chemical structures wherein $R^6$ is

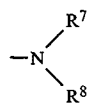

wherein $R^7$ and $R^8$ are organic radicals, or are joined to form an organic ring structure, or salts or hydrates thereof.

More preferred still are antibacterial nitrofurans conforming to the above chemical structures wherein $R^7$ is

wherein $R^9$ is H, lower alkyl, amine, amino(lower)alkyl, amide, hydroxy, or lower alkoxy; and wherein $R^8$ is H, lower alkyl, lower alkyl alcohol, or lower alkyl amine; or wherein $R^9$ and $R^8$ are joined such that $R^6$ is a five membered ring having the following chemical structure:

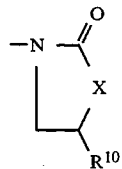

wherein $R^{10}$ is H, lower alkyl, $-CH_2N(H$ or lower alkyl$)_2$, or

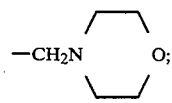

and X is O or $NR^{11}$, wherein $R^{11}$ is H, lower alky, or lower alkyl alcohol, or salts or hydrates thereof.

Antibacterial nitrofurans most preferred as components of the present invention include nitrofurantoin which has the chemical structure

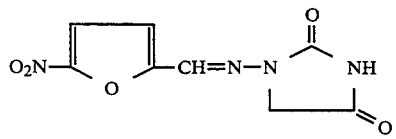

or its pharmaceutically-acceptable salts or hydrates; nitrofurazone which has the chemical structure:

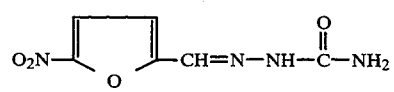

or its pharmaceutically-acceptable salts or hydrates; and furazolidone which has the chemical structure:

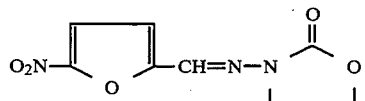

or its pharmaceutically-acceptable salts or hydrates.

Especially preferred is nitrofurantoin which is a well-known antibacterial compound and has been used extensively as an active ingredient in antibacterial pharmaceutical compositions. See, for example, Mintzer, S., E. R. Kadison, W. H. Shlaes & O. Felsenfeld, "Treatment of Urinary Tract Infections with a New Antibacterial Nitrofuran", *Antibiotics & Chemotherapy*, Vol. 3, No. 2 (February, 1953), pp. 151–157; Richards, W. A., E. Riss, E. H. Kass & M. Finland, "Nitrofurantoin— Clinical and Laboratory Studies in Urinary Tract Infections", *Archives of Internal Medicine*, Vol. 96 (1955], pp. 437–450; Eudy, W. W., "Correlations Between In Vitro Sensitivity Testing and Therapeutic Response in Urinary Tract Infections", *Urology*, Vol. II, No. 5, (November, 1973), pp. 519–587; Bush, I.M., W.I. Metzger, I. Garlovsky, R. B. Bush, R. J. Ablin 6 N. Sadoughi, "Urinary Tract Infection—Antibacterial Susceptability Patterns", Urology, Vol. III, No. 6 (June, 1974), pp. 697–700; Dickey, L., "A Comparison of the In Vitro Effectiveness of Nitrofurantoin and Five Antibiotics Against Bacteria from Urinary Tract Infections", *American Journal of Medical Technology*, (September-October, 1961), pp. 273–279; Karmali, M. A., S. DeGrandis & P. C. Fleming, "Antimicrobial Susceptibility of *Campylobacter jejuni* with Special Reference to Resistance Patterns of Canadian Isolates", *Antimicrobial Agents and Chemotherapy*, Vol. 19, No. 4 (1981), pp. 593–597.

Antibiotics are also among the preferred campylobacter-inhibiting antimicrobial agents useful herein. Such antibiotics can be generally classified by chemical composition into the following principal groups: the aminoglycosides, such as gentamicin, neomycin, kanamycin, and streptomycin; the macrolides, such as erythromycin, clindamycin, and rifampin; the penicillins, such as penicillin G, penicillin V, ampicillin, and amoxycillin; the polypeptides, such as bacitracin and polymyxin; the tetracyclines, such as tetracycline, chlortetracycline, oxytetracycline, and doxycycline; the cephalosporins, such as cephalexin and cephalothin; and such miscellaneous antibiotics and chloramphenicol and clindamycin. These antibiotics can be generally said to function in one of four ways: inhibition of cell wall synthesis, alteration of cell wall permeability, inhibition of protein synthesis, or inhibition of nucleic acid synthesis.

Campylobacter-inhibiting bismuth-containing agents (as disclosed in the concurrently filed, copending patent application of G. Place having U.S. patent application Ser. No. 023,597, incorporated by reference herein in its entirety) are also preferred campylobacter-inhibiting antimicrobial agents for use herein. Preferred campylobacter-inhibiting bismuth-containing agents are bismuth subcitrate and bismuth subsalicylate.

Specific campylobacter-inhibiting antimicrobial agents useful herein are: penicillin G, mezlocillin, ampicillin, cefalothin, cefoxitin, cefotaxime, imipenem, gentamicin, amikacin, erythromycin, ciprofloxacin, tetracyclines, metronidazole, amoxycillin, cephalosporins, nitrofurantoin, nitrofurazone, furazolidone, bismuth subsalicylate, and bismuth subcitrate. The most preferred campylobactor-inhibiting antimicrobial agents for use herein is nitrofurantoin.

The pharmaceutical compositions of the present invention typically comprise, by weight, from about 0.1% to about 99.8% of the campylobacter-inhibiting antimicrobial agent, preferably from about 0.1% to about 75%, and most preferably from about 1% to about 50%.

$H_2$ Receptor Blocking Anti-Secretory Agents

In addition to the bismuth-containing agent described hereinbefore, the pharmaceutical compositions of the present invention also comprise an $H_2$ receptor blocking anti-secretory agent. The $H_2$ receptor blocking anti-secretory agents useful in the present invention include cimetidine, ranitidine, burimamide, metiamide, tiotidine, and oxmetidine, as well as compounds of the formula:

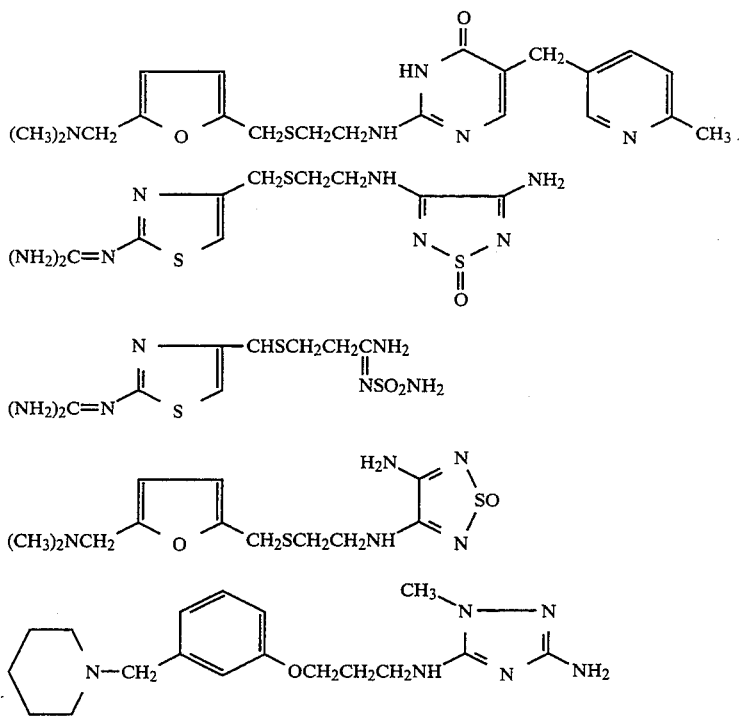

The above structures are well-known in the art (see C & E News, Apr. 12, 1982, pp 24–26, expressly incorporated herein by reference in its entirety). Mixtures of the above H2 receptor blocking anti-secretory agents may also be employed. The most preferred of these compounds are cimetidine, ranitidine, and mixtures thereof, with cimetidine being especially preferred.

The preparation and use of H2 receptor blocking anti-secretory agents as described hereinbefore are well-known in the art. For example, the preparation and use of cimetidine are discussed in U.S. Pat. No. 3,950,333, to Durant et al., issued Apr. 13, 1976; Brimblecombe, et al., *J. Int. Med. Res.*, 3, 86 (1975); Brimblecombe, et al., *Brit. J. Pharmacol.*, 53, 435 (1975); and Brogden, et al., *Drugs*, 15, 93–131 (1978); the disclosures of these patents and articles being incorporated herein by reference in their entirety. Also, for example, the preparation and use of ranitidine are discussed in U.S. Pat. No. 4,128,658, to Price et al., issued Dec. 5, 1978; Bradshaw et al., *Brit. J. Pharmacol.*, 66, 464 (1979); Daly, et al., Gut, 21, 408 (1980); Berstad, et al., *Scand. J. Gastroenterol.*, 15, 637 (1980); and Wait, et al., *Gut*, 22, 49 (1981); the disclosures of these patents and articles being incorporated herein by reference in their entirety.

The pharmaceutical compositions of the present invention typically comprise, by weight, from about 0.1% to about 99.8% of the H2 receptor blocking anti-secretory agent, preferably from about 0.1% to about 75%, and most preferably from about 1% to about 50%.

Pharmaceutically-Acceptable Carriers

In addition to the campylobacter-inhibiting antimicrobial agent and the H2 receptor blocking anti-secretory agent as described hereinbefore, the pharmaceutical compositions of the present invention also essentially contain a pharmaceutically-acceptable carrier. The term "pharmaceutically-acceptable carrier", as used herein, means one or more compatible solid or liquid filler diluents or encapsulating substances which are suitable for administration to a human or lower animal. The term "compatible", as used herein, means that the components of the pharmaceutical composition are capable of being commingled with the campylobacter-inhibiting antimicrobial agent and the H2 receptor blocking anti-secretory agent, and with each other, in a manner such that there is no interaction which would substantially reduce the pharmaceutical efficacy of the pharmaceutical composition under ordinary use situations. Pharmaceutically-acceptable carriers must, of course, be of sufficiently high purity and sufficiently low toxicity to render them suitable for administration to the human or lower animal being treated.

A variety of pharmaceutically-acceptable carriers may be included, depending on the particular dosage form to be used. Various oral dosage forms can be used, including such solid forms as tablets, capsules, granules and bulk powders. Tablets can be compressed, tablet triturates, enteric-coated, sugar-coated, film-coated or multiple compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules and effervescent preparations reconstituted from effervescent granules, containing suitable solvents, preservatives, emulsifying agents, suspending agents, diluents, sweeteners, melting agents, coloring, and flavoring agents.

Some examples of substances which can serve as pharmaceutically-acceptably carriers are sugars such as lactose, glucose and sucrose; starches such as corn starch and potato starch; cellulose and its derivatives such as sodium carboxymethylcellulose, ethylcellulose, cellulose acetate; powdered tragacanth; malt; gelatin;

talc; stearic acid; magnesium stearate; calcium sulfate; vegetable oils such as peanut oil, cottonseed oil, sesame oil, olive oil, corn oil and oil of theobroma; polyois such as propylene glycol, glycerine, sorbitol, mannitol, and polyethylene glycol; agar; alginic acid; pyrogen-free water; isotonic saline; and phosphate buffer solutions, as well as other non-toxic compatible substances used in pharmaceutical formulations. Wetting agents and lubricants such as sodium lauryl sulfate, as well as coloring agents, flavoring agents, excipients, tableting agents, stabilizers, anti-oxidants, and preservatives can also be present. Other compatible pharmaceutical additives and actives (e.g., NSAI drugs; pain killers; muscle relaxants) may be included in the pharmaceutically-acceptable carrier for use in the compositions of the present invention.

Specific examples of pharmaceutically-acceptable carriers that may be used to formulate oral dosage forms of the present invention are described in U.S. Pat. No. 3,903,297, Robert, issued Sep. 2, 1975, incorporated by reference herein in its entirety. Techniques and compositions for making dosage forms useful herein are described in the following references, all incorporated by reference herein in their entirety: 7 *Modern Pharmaceuticals*, Chapters 9 and 10 (Banker and Rhodes, Ed., 1979); Lieberman, et al., *Pharmaceutical Dosage Forms: Tablets* (1981); and Ansel, *Introduction to Pharmaceutical Dosage Forms* (2nd Edition, 1976).

The choice of a pharmaceutically-acceptable carrier to be used in conjunction with the campylobacter-inhibiting antimicrobial agent and $H_2$ receptor blocking anti-secretory agent combination of the present invention is basically determined by the way the composition is to be administered. The preferred mode of administering the compositions of the present invention is orally. The preferred unit dosage form is therefore tablets, capsules, and the like, comprising a safe and effective amount of the campylobacter-inhibiting antimicrobial agent and the $H_2$ receptor blocking anti-secretory agent combination of the present invention. Pharmaceutically-acceptable carriers suitable for the preparation of unit dosage forms for oral administration are well known in the art. Their selection will depend on secondary considerations like taste, cost, shelf stability, which are not critical for the purposes of the present invention, and can be made without difficulty by a person skilled in the art.

The pharmaceutically-acceptable carrier employed in conjunction with the campylobacter-inhibiting antimicrobial agent and the $H_2$ receptor blocking anti-secretory agent combination of the present invention is used at a concentration sufficient to provide a practical size to dosage relationship. The pharmaceutically-acceptable carriers, in total, may comprise from about 0.1% to about 99.8%, by weight, of the pharmaceutical compositions of the present invention, preferably from about 25% to about 99.8%, and most preferably from about 50% to about 99%.

Methods for Treating or Preventing Gastrointestinal Disorders

Another aspect of the present invention is methods for treating or preventing gastrointestinal disorders. Such methods comprise administering, to a human or lower animal in need of such treatment or prevention, a safe and effective amount of a campylobacter-inhibiting antimicrobial agent and safe and effective amount of a $H_2$ receptor blocking anti-secretory agent.

The term "administering", as used herein, refers to any method which, in sound medical practice, delivers the campylobacter-inhibiting antimicrobial agent and the $H_2$ receptor blocking anti-secretory agent to the subject to be treated in such a manner so as to be effective in the treatment of the gastrointestinal disorder. Preferably, both these agents are administered orally.

The term "gastrointestinal disorder", as used herein, encompasses any disease or other disorder of the upper gastrointestinal tract of a human or lower animal. The term "upper gastrointestinal tract", as used herein, is defined to include the esophagus, the stomach, the duodenum, and the jejunum. Such gastrointestinal disorders include, for example: disorders not manifested by presence of ulcerations in the gastric mucosa (herein "non-ulcerative gastrointestinal disorders"), including chronic or atrophic gastritis, non-ulcer dyspepsia, esophageal reflux disease and gastric motility disorders; and "peptic ulcer disease", i.e., gastric, duodenal and jejunal ulcers. Gastrointestinal disorder especially refers to such disorders of the upper gastrointestinal tract which are conventionally treated with $H_2$ receptor blocking anti-secretory agents alone.

The phrase "safe and effective amount", as used herein, means an amount of a campylobacter-inhibiting antimicrobial agent or $H_2$ receptor blocking anti-secretory agent, when used in combination with each other according to the compositions and methods of the present invention, high enough to significantly positively modify the condition to be treated but low enough to avoid serious side effects (at a reasonable benefit/risk ratio), within the scope of sound medical judgment. The safe and effective amount of the agents of the present invention will vary with the particular condition being treated, the age and physical condition of the patient being treated, the severity of the condition, the duration of treatment, the nature of concurrent therapy, the specific agents employed, the particular pharmaceutically-acceptable carrier utilized, and like factors within the knowledge and expertise of the attending physician.

The methods of the present invention typically involve administering the campylobacter-inhibiting antimicrobial agent in an amount of from about 1 mg to about 10,000 mg of antimicrobial agent per day. The specific preferred quantity of antimicrobial depends upon the particular antimicrobial used and its pharmacology. In general, though, the tetracyclines are preferably administered at a level of from about 100 mg to about 2000 mg per day. Macrolides (such as erythromycin) are preferably administered at a level of from about 1000 mg to about 4000 mg per day. Penicillins are preferrably administered at a level of from about 500 mg to about 3000 mg per day. The aminoglycosides (such as neomycin) are, preferably, administered at a level of from about 100 mg to about 8000 mg per day. Preferably, metronidazole is administered at a level of from about 500 mg to about 2000 mg per day. Nitrofurans (such as nitrofurantoin) are administered preferably at a level of from about 1 mg to about 800 mg per day. More particularly, the preferred daily dosage of nitrofurantoin is from about 1 mg to about 600 mg per day, more preferably from about 10 mg to about 400 mg per day, and most preferably from about 20 mg to about 200 mg per day.

The method of the present invention typically involves administering the $H_2$ receptor blocking anti-secretory agent in an amount of from about 1 mg to about 10 g per day. Preferably from about 50 mg to about 5000 mg, more preferably from about 100 mg to about 1500 mg, most preferably from about 400 mg to about 1200 mg, of cimetidine is administered per day.

The methods of the present invention comprise administering the campylobacter-inhibiting antimicrobial agent and the $H_2$ receptor blocking anti-secretory agent either concurrently or non-concurrently. The term "concurrently", as used herein, means that the two agents are administered within 24 hours or less of each other, preferably within about 12 hours of each other, more preferably within about 1 hour of each other, and most preferably within about 5 minutes of each other; and includes co-administration of the agents by administering a composition of the present invention. The term "non-concurrently", as used herein, means that the two agents are administered more than 24 hours apart.

The methods of the present invention in which the agents are administered concurrently comprise any dosing regimen in which part or all of the dosing of the agents is preformed concurrently. Thus, for example, methods comprising concurrent dosing of the agents include:

1. 14 days of administration of a pharmaceutical composition of the present invention.
2. 21 days of a regimen wherein the campylobacter-inhibiting antimicrobial agent is administered in the morning and the $H_2$ receptor blocking anti-secretory agent is administered at night (approximately 12 hours apart).
3. 28 days of administration of the campylobacter-inhibiting antimicrobial agent and the $H_2$ receptor blocking anti-secretory agent essentially simultaneously (i.e., within about 5 minutes of each other), followed by 7 days of treatment with only the campylobacter-inhibiting antimicrobial agent.
4. 3 days of administration of only the campylobacter-inhibiting antimicrobial agent, followed by 21 days of administration of the campylobacter-inhibiting antimicrobial agent and the $H_2$ receptor blocking anti-secretory agent essentially simultaneously (i.e., within about 5 minutes of each other).

The methods of the present invention in which the agents are administered non-concurrently comprise any dosing regimen in which none of the dosing of the agents is performed concurrently. Thus, for example, methods comprising non-concurrent dosing of the agents include:

1. 28 days of alternating daily dosing of the campylobacter-inhibiting antimicrobial agent and the $H_2$ receptor blocking anti-secretory agent, starting with the $H_2$ receptor blocking anti-secretory agent and ending with the campylobacter-inhibiting antimicrobial agent.
2. 14 days of administration of the $H_2$ receptor blocking anti-secretory agent followed by 14 days of administration of the campylobacter-inhibiting antimicrobial agent.
3. 7 days of administration of the campylobacter-inhibiting antimicrobial agent, followed by 14 days of administration of the $H_2$ receptor blocking anti-secretory agent.

For the methods of the present invention, the duration of administration of the agents during either concurrent or non-concurrent dosing of the agents will vary according to the specific gastrointestinal disorder being treated, but typically is within the range of from about 1 to about 60 days. In general, however, in methods for treatment of non-ulcerative gastrointestinal disorders the duration of treatment comprises administering the agents for from about 3 to about 21 days. In methods for treatment of peptic ulcer disease, the duration of treatment comprises administering the agents for from about 14 to about 56 days. If the compositions of the present application are administered, similar durations are utilized depending on the gastrointestinal disorder to be treated.

The following examples further describe and demonstrate the preferred embodiments within the scope of the present invention. The examples are given solely for the purpose of illustration, and are not to be construed as limitations of the present invention since many variations thereof are possible without departing from its spirit and scope.

EXAMPLE I

Pharmaceutical Compositions in Tablet Form

Tablets are prepared by conventional methods, such as mixing and direct compaction, formulated as follows:

| Ingredients | Mg per Tablet |
| --- | --- |
| Nitrofurantoin | 50 |
| Cimetidine | 300 |
| Microcrystalline cellulose | 100 |
| Sodium starch glycolate | 30 |
| Magnesium stearate | 3 |

When one tablet is administered orally 4 times per day for 14 days, the above compositions significantly improve the condition of a patient suffering from gastritis. A significant long-lasting benefit is also acheived by daily administration for 28 days (4 tablets per day) of this composition to a patient suffering from gastric ulcers. Similar results are achieved with tablets formulated as above but replacing the cimetidine with ranitidine.

EXAMPLE II

Pharmaceutical Compositions in Capsule Form

Capsules are prepared by conventional methods, comprised as follows:

| Ingredients | Mg/Capsule |
| --- | --- |
| Nitrofurantoin | 50 |
| Cimetidine | 300 |
| Lactose | To fill to volume of capsule |

One of the above capsules administered orally 4 times a day for 21 days substantially reduces the symptomology of a patient afflicted with a gastric ulcer. Similar results are obtained with capsules formulated above but replacing the cimetidine with ranitidine.

EXAMPLE III

Methods Comprising Concurrent Administration

A patient suffering from gastritis is treated according to a regimen comprising 28 days of oral administration of 200 mg of nitrofurantoin in the morning and oral administration of 400 mg of cimetidine (as 2 Tagamet ® tablets; sold by Smith Kline and French Laboratories) in the evening before bedtime. This regimen significantly improves the condition of the patient being treated. Similar results are obtained when the cimetidine is replaced with ranitidine.

Similarly effective treatment of a patient suffering from gastritis is achieved by the following regimens utilizing nitrofurantoin and cimetidine (supplied as Tagamet ®): 21 days of daily oral administration of the two agents within about 5 minutes of each other; 21 days of daily oral administration of the two agents within about 5 minutes of each other followed by 7 days of treatment with only nitrofurantoin; and 7 days of treatment with nitrofurantoin followed by 21 days of daily oral administration of the two agents within about 5 minutes of each other.

EXAMPLE IV

Methods Comprising Non-concurrent Administration

A patient suffering from gastritis is treated according to a regimen comprising 29 days of alternating daily oral dosing of 100 mg of nitrofurantoin, and 400 mg of cimetidine (as 2 Tagamet ® tablets; sold by the Smith Kline and French Laboratories), with the treatment regimen beginning on day 1 with administration of the nitrofurantoin, and alternating the agents daily through day 29 which is also the administration of nitrofurantoin. This regimen significantly improves the condition of the patient being treated.

Similarly effective treatment of a patient suffering from gastritis is achieved by the following regimens utilizing nitrofurantoin and cimetidine: 14 days of daily oral administration of cimetidine, followed by 14 days of daily oral administration of nitrofurantoin; 7 days of daily oral administration of nitrofurantoin, followed by 14 days of daily oral administration of cimetidine; and 7 days of daily oral administration of nitrofurantoin, followed by 14 days of daily oral administration of cimetidine, followed by 7 days of daily oral administration of nitrofurantoin.

What is claimed is:

1. Pharmaceutical compositions useful for treating or preventing gastrointestinal disorders, said compositions comprising:
   (a) a safe and therapeutically effective amount of a campylobacter-inhibiting antimicrobial agent;
   (b) a safe and therapeutically effective amount of an $H_2$ receptor blocking anti-secretory agent; and
   (c) a pharmaceutically-acceptable carrier.

2. Pharmaceutical compositions useful for treating or preventing gastrointestinal disorders, according to claim 1, wherein the campylobacter-inhibiting antimicrobial agent is selected from the group consisting of antibacterial nitrofurans and antibiotics.

3. Pharmaceutical compositions useful for treating or preventing gastrointestinal disorders, according to claim 2, wherein the campylobacter-inhibiting antimicrobial agent is nitrofurantoin.

4. Pharmaceutical compositions useful for treating or preventing gastrointestinal disorders, according to claim 2, wherein the $H_2$ receptor blocking anti-secretory agent is selected from the group consisting of cimetidine, ranitidine, and mixtures thereof.

5. Pharmaceutical compositions useful for treating or preventing gastrointestinal disorders, said compositions comprising:
   (a) a safe and therapeutically effective amount of nitro-furantoin;
   (b) a safe and therapeutically effective amount of an $H_2$ receptor blocking anti-secretory agent selected from the group consisting of cimetidine, ranitidine, and mixtures thereof; and
   (c) a pharmaceutically-acceptable carrier.

6. Pharmaceutical compositions useful for treating or preventing gastrointestinal disorders, according to claim 5, wherein the $H_2$ receptor blocking anti-secretory agent is cimetidine.

7. Methods for treating or preventing gastrointestinal disorders in humans or lower animals, said methods comprising administering to a human or lower animal in need of such treatment or prevention a safe and therapeutically effective amount of a campylobacter-inhibiting antimicrobial agent and a safe and therapeutically effective amount of an $H_2$ receptor blocking anti-secretory agent, except that when said methods are methods whereby only a bismuth-containing campylobacter-inhibiting antimicrobial agent is administered with an $H_2$ receptor blocking anti-secretory agent, then said methods further comprise administering the bismuth-containing campylobacter-inhibiting antimicrobial agent and an H2 receptor blocking anti-secretory agent within about one hour of each other.

8. A method for treating or preventing gastrointestinal disorders in humans or lower animals, according to claim 7, wherein the campylobacter-inhibiting antimicrobial agent and the $H_2$ receptor blocking anti-secretory agent are both administered orally and concurrently.

9. A method for treating or preventing gastrointestinal disorders in humans or lower animals, according to claim 8, wherein the campylobacter-inhibiting antimicrobial agent and the $H_2$ receptor blocking anti-secretory agent are administered concurrently.

10. Methods for treating or preventing gastrointestinal disorders in humans or lower animals, according to claim 9, wherein the campylobacter-inhibiting antimicrobial agent is selected from the group consisting of antibacterial nitrofurans and antibiotics.

11. Methods for treating or preventing gastrointestinal disorders in humans or lower animals, according to claim 10, wherein the campylobacter-inhibiting antimicrobial agent is nitrofurantoin; and wherein further the $H_2$ receptor-blocking anti-secretory agent is selected from the group consisting of cimetidine, ranitidine, and mixtures thereof.

12. Methods for treating or preventing gastrointestinal disorders in humans or lower animals, according to claim 11, wherein the campylobacter-inhibiting antimicrobial agent is nitrofurantoin, and the $H_2$ receptor blocking anti-secretory agent is cimetidine.

13. Methods for treating or preventing gastrointestinal disorders in humans or lower animals, according to claim 8, wherein the campylobacter-inhibiting antimicrobial agent and the $H_2$ receptor blocking anti-secretory agent are administered non-concurrently.

14. Methods for treating or preventing gastrointestinal disorders in humans or lower animals, according to claim 13, wherein the campylobacter-inhibiting antimicrobial agent is selected from the group consisting of antibacterial nitrofurans and antibiotics.

15. Methods for treating or preventing gastrointestinal disorders in humans or lower animals, according to claim 14, wherein the campylobacter-inhibiting antimicrobial agent is nitrofurantoin; and wherein further the $H_2$ receptor blocking anti-secretory agent is selected from the group of cimetidine, ranitidine, and mixtures thereof.

16. Methods for treating or preventing gastrointestinal disorders in humans or lower animals, according to claim 15, wherein the campylobacter-inhibiting antimicrobial agent is nitrofurantoin, and the $H_2$ receptor blocking anti-secretory agent is cimetidine.

17. Methods for treating or preventing gastrointestinal disorders in humans or lower animals, said methods comprising administering to a human or lower animal in need of such treatment or prevention a safe and therapeutically effective amount of a pharmaceutical composition according to claim 1.

18. Methods for treating or preventing gastrointestinal disorders in humans or lower animals, said methods comprising administering to a human or lower animal in need of such treatment or prevention a safe and therapeutically effective amount of a pharmaceutical composition according to claim 3.

19. Methods for treating or preventing gastrointestinal disorders in humans or lower animals, said methods comprising administering to a human or lower animal in need of such treatment or prevention a safe and therapeutically effective amount of a pharmaceutical composition according to claim 5.

20. Methods for treating or preventing gastrointestinal disorders in humans or lower animals, said methods comprising administering to a human or lower animal in need of such treatment or prevention a safe and therapeutically effective amount of a pharmaceutical composition according to claim 6.

21. Pharmaceutical compositions useful for treating or preventing gastrointestinal disorders, said compositions comprising:
(a) a safe and therapeutically effective amount of a campylobacter-inhibiting antimicrobial agent; and
(b) a safe and therapeutically effective amount of a pharmaceutically-acceptable salt suitable for oral co-administration of a bismuth-containing agent and an $H_2$ receptor blocking anti-secretory agent, said salt comprising bismuth, an organic acid, and an $H_2$ receptor blocking anti-secretory agent selected from the group consisting of ranitidine and cimetidine.

22. Pharmaceutical compositions according to claim 21 wherein said organic acid is selected from the group consisting of citrate and tartrate.

23. Pharmaceutical compositions according to claim 22 wherein said pharmaceutically-acceptable salt comprises bismuth, citrate and ranitidine.

24. Pharmaceutical compositions according to claim 22 wherein said pharmaceutically-acceptable salt comprises bismuth, citrate and cimetidine.

25. Pharmaceutical compositions according to claim 22 wherein said pharmaceutically-acceptable salt comprises bismuth, tartrate and ranitidine.

26. Pharmaceutical compositions according to claim 22 wherein said pharmaceutically-acceptable salt comprises bismuth, tartrate and cimetidine.

27. A method for treating or preventing gastrointestinal disorders in humans or lower animals, said method comprising orally administering to a human or lower animal in need of such treatment or prevention a safe and therapeutically effective amount of a pharmaceutical composition according to claim 21.

28. A method for treating or preventing gastrointestinal disorders in humans or lower animals, said method comprising orally administering to a human or lower animal in need of such treatment or prevention a safe and therapeutically effective amount of a pharmaceutical composition according to claim 22.

29. A method for treating or preventing gastrointestinal disorders in humans or lower animals, said method comprising orally administering to a human or lower animal in need of such treatment or prevention a safe and therapeutically effective amount of a pharmaceutical composition according to claim 23.

30. A method for treating or preventing gastrointestinal disorders in humans or lower animals, said method comprising orally administering to a human or lower animal in need of such treatment or prevention a safe and therapeutically effective amount of a pharmaceutical composition according to claim 24.

31. A method for treating or preventing gastrointestinal disorders in humans or lower animals, said method comprising orally administering to a human or lower animal in need of such treatment or prevention a safe and therapeutically effective amount of a pharmaceutical composition according to claim 25.

32. A method for treating or preventing gastrointestinal disorders in humans or lower animals, said method comprising orally administering to a human or lower animal in need of such treatment or prevention a safe and therapeutically effective amount of a pharmaceutical composition according to claim 26.

33. A method for treating or preventing gastrointestinal disorders in humans or lower animals, said method comprising dosing the gastrointestinal tract of the human or lower animal in need of such treatment or prevention with safe and therapeutically effective amounts of bismuth, ranitidine, and a non-bismuth campylobacter-inhibiting antimicrobial agent.

34. A method for treating or preventing gastrointestinal disorders according to claim 33 wherein the bismuth, ranitidine, and non-bismuth campylobacter-inhibiting antimicrobial agent are administered concurrently.

35. A method for treating or preventing gastrointestinal disorders according to claim 33 wherein at least one of the bismuth, ranitidine and non-bismuth campylobacter-inhibiting antimicrobial agent are administered non-concurrently.

36. A method for treating or preventing gastrointestinal disorders in humans or lower animals, said method comprising dosing the gastrointestinal tract of the human or lower animal in need of such treatment or prevention with safe and therapeutically effective amounts of bismuth, cimetidine, and a non-bismuth campylobacter-inhibiting antimicrobial agent.

37. A method for treating or preventing gastrointestinal disorders according to claim 36 wherein the bismuth, cimetidine, and non-bismuth campylobacter-inhibiting antimicrobial agent are administered concurrently.

38. A method for treating or preventing gastrointestinal disorders according to claim 36 wherein at least one of the bismuth, cimetidine and non-bismuth campylobacter-inhibiting antimicrobial agent are administered non-concurrently.

39. A method for treating ulcers of the upper gastrointestinal tract in humans or lower animals, said method comprising concurrently treating the upper gastrointestinal tract of the human or lower animal in need of such treatment with safe and therapeutically effective amounts of bismuth, ranitidine, and a non-bismuth campylobacter-inhibiting antimicrobial agent.

40. A method for treating ulcers of the upper gastrointestinal tract in humans or lower animals, said method comprising concurrently treating the upper gastrointestinal tract of the human or lower animal in need of such treatment with safe and therapeutically effective amounts of bismuth, cimetidine, and a non-bismuth campylobacter-inhibiting antimicrobial agent.

41. A method for treating non-ulcerative gastrointestinal disorders in humans or lower animals, said method comprising concurrently treating the upper gastrointestinal tract of the human or lower animal in need of such treatment with safe and therapeutically effective amounts of bismuth, ranitidine, and a non-bismuth campylobacter-inhibiting antimicrobial agent.

42. A method for treating non-ulcerative gastrointestinal disorders in humans or lower animals, said method comprising concurrently treating the upper gastrointestinal tract of the human or lower animal in need of such treatment with safe and therapeutically effective amounts of bismuth, cimetidine, and a non-bismuth campylobacter-inhibiting antimicrobial agent.

43. A method for treating *Campylobacter pyloridis* infection of the upper gastrointestinal tract in humans or lower animals, said method comprising concurrently treating the upper gastrointestinal tract of the human or lower animal infected with *Campylobacter pyloridis* with safe and therapeutically effective amounts of bismuth, ranitidine, and a non-bismuth campylobacter-inhibiting antimicrobial agent.

44. A method for treating *Campylobacter pyloridis* infection of the upper gastrointestinal tract in humans or lower animals, said method comprising concurrently treating the upper gastrointestinal tract of the human or lower animal infected with *Campylobacter pyloridis* with safe and therapeutically effective amounts of bismuth, cimetidine, and a non-bismuth campylobacter-inhibiting antimicrobial agent.

45. Methods for treating or preventing gastrointestinal disorders in human or lower animals, said methods comprising administering to a human or lower animal in need of such treatment or prevention a safe and therapeutically effective amount of a campylobacter-inhibiting antimicrobial agent and a safe and therapeutically effective amount of an $H_2$ receptor blocking anti-secretory agent, except that when said methods are methods whereby only a bismuth-containing campylobacter-inhibiting antimocrobial agent is administered with an $H_2$ receptor blocking anti-secretory agent, then said methods further comprise administering the bismuth-containing campylobacter-inhibiting antimicrobial agent and an $H_2$ receptor blocking anti-secretory agent within about five minutes of each other.

* * * * *